(12) United States Patent
Hutson et al.

(10) Patent No.: US 8,292,865 B2
(45) Date of Patent: Oct. 23, 2012

(54) ABSORBENT ARTICLE WITH DOUBLE-SIDED SOFT AND ELASTIC COMPONENTS

(75) Inventors: Randell O. Hutson, Terre Haute, IN (US); Andrew J. Peacock, Terre Haute, IN (US)

(73) Assignee: Tredegar Film Products Corporation, Richmond, VA (US)

( * ) Notice: Subject to any disclaimer, the term of this patent is extended or adjusted under 35 U.S.C. 154(b) by 2162 days.

(21) Appl. No.: 10/308,703

(22) Filed: Dec. 2, 2002

(65) Prior Publication Data

US 2003/0105446 A1    Jun. 5, 2003

Related U.S. Application Data

(60) Provisional application No. 60/334,913, filed on Nov. 30, 2001.

(51) Int. Cl.
*A61F 13/15*    (2006.01)

(52) U.S. Cl. ......... 604/385.27; 604/385.24; 604/385.26; 604/385.01; 604/385.23; 604/385.3

(58) Field of Classification Search ............. 604/385.27, 604/385.24, 385.26, 385.01, 385.23, 385.3
See application file for complete search history.

(56) References Cited

U.S. PATENT DOCUMENTS

| | | | |
|---|---|---|---|
| 1,938,318 A | 12/1933 | Colby | 164/99 |
| 2,896,626 A | 7/1959 | Voigtman | 128/287 |
| 3,657,940 A | 4/1972 | Wagner | 74/397 |
| 4,082,877 A | 4/1978 | Shadle | |
| 4,107,364 A | 8/1978 | Sisson | |
| 4,116,892 A | 9/1978 | Schwarz | 521/62 |
| 4,223,059 A | 9/1980 | Schwarz | 428/198 |
| 4,223,063 A | 9/1980 | Sabee | |
| 4,374,888 A | 2/1983 | Bornslaeger | 428/198 |
| 4,446,189 A | 5/1984 | Romanek | 428/152 |
| 4,515,595 A | 5/1985 | Kievit et al. | |
| 4,525,407 A | 6/1985 | Ness | |
| 4,578,024 A | 3/1986 | Sicka et al. | |
| 4,816,094 A | 3/1989 | Pomplun et al. | |
| 4,834,741 A | 5/1989 | Sabee | |
| 4,857,409 A | 8/1989 | Hazelton et al. | |
| 4,880,682 A | 11/1989 | Hazelton et al. | |
| 5,037,416 A | 8/1991 | Allen et al. | 604/385.1 |

(Continued)

FOREIGN PATENT DOCUMENTS

EP    0020083    5/1980

(Continued)

OTHER PUBLICATIONS

International Search Report for PCT/US 02/38388 dated May 6, 2003.

*Primary Examiner* — Jacqueline F. Stephens
(74) *Attorney, Agent, or Firm* — Condo Roccia LLP

(57) ABSTRACT

The present invention relates to absorbent articles and non-absorbent articles which comprise at least one improved double-sided soft and elastic material composite. The composites according to the invention may also be breathable. The composites are produced by incrementally stretching a laminate of an elastic layer between two non-elastic cloth-like layers. The non-elastic cloth-like layers tear during stretching such that the elasticity of the laminate after stretching is substantially the same as the elasticity of the film elastic layer.

36 Claims, 3 Drawing Sheets

U.S. PATENT DOCUMENTS

| | | | |
|---|---|---|---|
| 5,143,679 A | 9/1992 | Weber et al. | 264/288.8 |
| 5,151,092 A | 9/1992 | Buell et al. | |
| 5,156,793 A | 10/1992 | Buell et al. | |
| 5,167,879 A | 12/1992 | Streng | 261/112.2 |
| 5,167,897 A | 12/1992 | Weber et al. | |
| 5,221,274 A | 6/1993 | Buell et al. | |
| 5,241,031 A | 8/1993 | Mehta | 526/348.1 |
| 5,244,482 A | 9/1993 | Hassenboehler, Jr. et al. | 55/528 |
| 5,344,691 A | 9/1994 | Hanschen et al. | |
| 5,376,430 A | 12/1994 | Swenson et al. | |
| 5,422,172 A | 6/1995 | Wu | 428/230 |
| 5,457,161 A | 10/1995 | Coolbaugh et al. | |
| 5,496,298 A | 3/1996 | Kuepper et al. | |
| 5,499,978 A | 3/1996 | Buell et al. | |
| 5,501,679 A | 3/1996 | Krueger et al. | |
| 5,527,304 A | 6/1996 | Buell et al. | 604/385.2 |
| 5,529,830 A * | 6/1996 | Dutta et al. | 428/176 |
| 5,591,278 A | 1/1997 | Marcu | 152/152.1 |
| 5,592,690 A | 1/1997 | Wu | 2/67 |
| 5,620,780 A | 4/1997 | Krueger et al. | |
| 5,628,741 A | 5/1997 | Buell et al. | 604/385.2 |
| 5,634,216 A | 6/1997 | Wu | 2/239 |
| 5,653,704 A | 8/1997 | Buell et al. | 604/385.2 |
| 5,674,216 A | 10/1997 | Buell et al. | 604/385.2 |
| 5,680,653 A * | 10/1997 | Mathis et al. | 2/123 |
| 5,690,627 A | 11/1997 | Clear et al. | 604/385.2 |
| 5,691,034 A | 11/1997 | Krueger et al. | |
| 5,723,087 A | 3/1998 | Chappell et al. | |
| 5,733,628 A | 3/1998 | Pelkie | 428/138 |
| 5,773,374 A | 6/1998 | Wood et al. | |
| 5,861,074 A | 1/1999 | Wu | 156/229 |
| 5,921,973 A | 7/1999 | Newkirk et al. | |
| 5,932,497 A * | 8/1999 | Morman et al. | 442/286 |
| 6,051,094 A | 4/2000 | Melbye et al. | |
| 6,069,097 A | 5/2000 | Suzuki et al. | |
| 6,159,584 A | 12/2000 | Eaton et al. | |
| 6,255,236 B1 * | 7/2001 | Cree et al. | 442/328 |
| 6,410,129 B2 | 6/2002 | Zhang et al. | 428/318.6 |
| 6,436,529 B1 | 8/2002 | Deeb et al. | |
| 6,452,063 B1 | 9/2002 | Curro et al. | 604/383 |
| 6,476,289 B1 | 11/2002 | Buell et al. | 604/367 |
| 6,531,207 B1 | 3/2003 | Eaton et al. | |

FOREIGN PATENT DOCUMENTS

| | | |
|---|---|---|
| EP | 0214608 | 9/1986 |
| EP | 0 685 586 A2 | 5/1995 |
| GB | 423828 | 2/1935 |
| GB | 484929 | 5/1938 |
| JP | 3 119 443 | 10/2000 |
| JP | 3 222 798 | 8/2001 |
| WO | WO 97/19662 | 6/1997 |

* cited by examiner

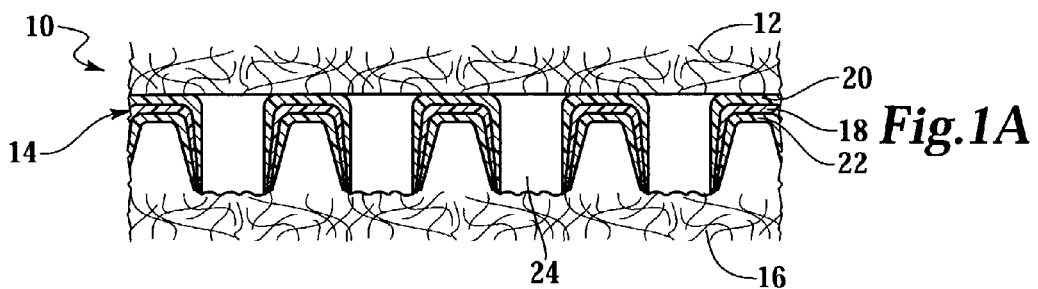
*Fig.1A*
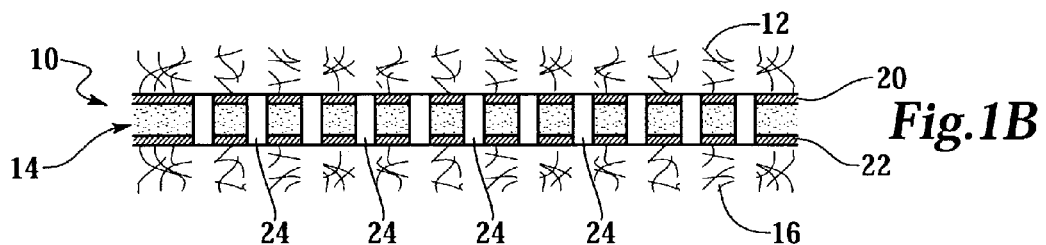
*Fig.1B*
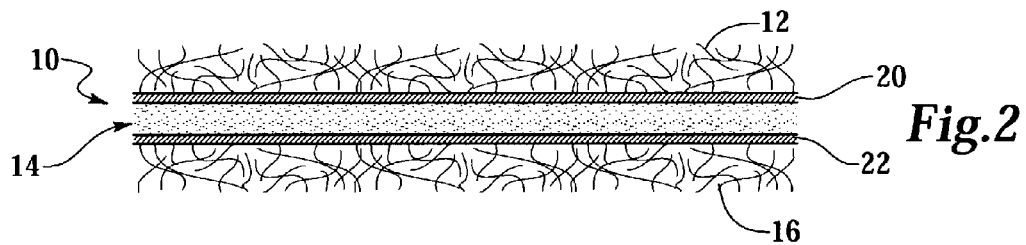
*Fig.2*
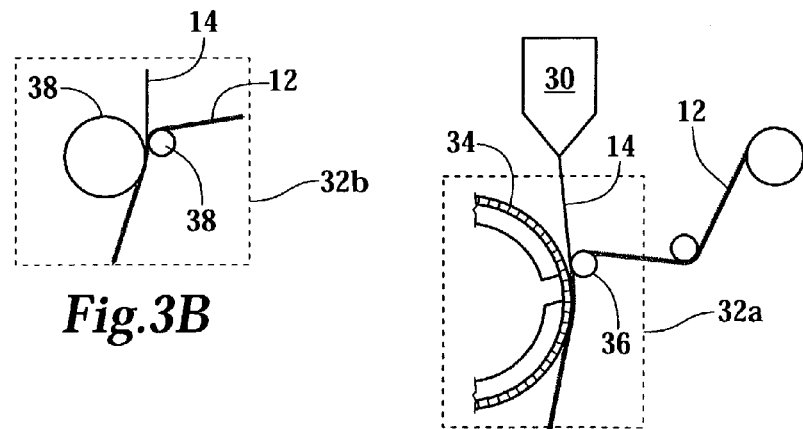
*Fig.3B*
*Fig.3A*

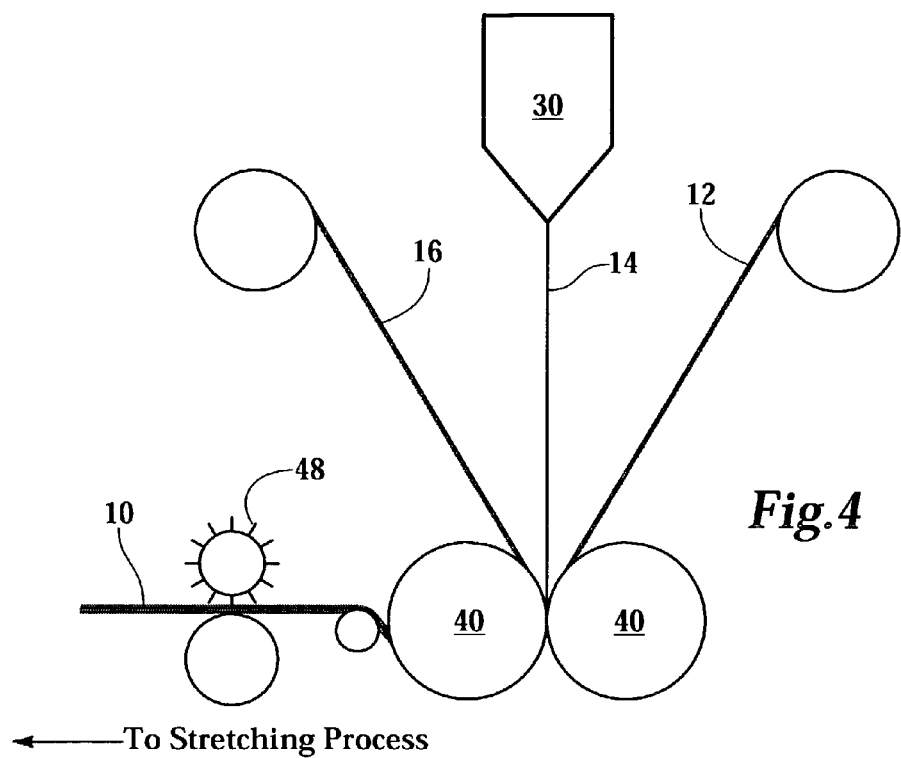
*Fig.4*
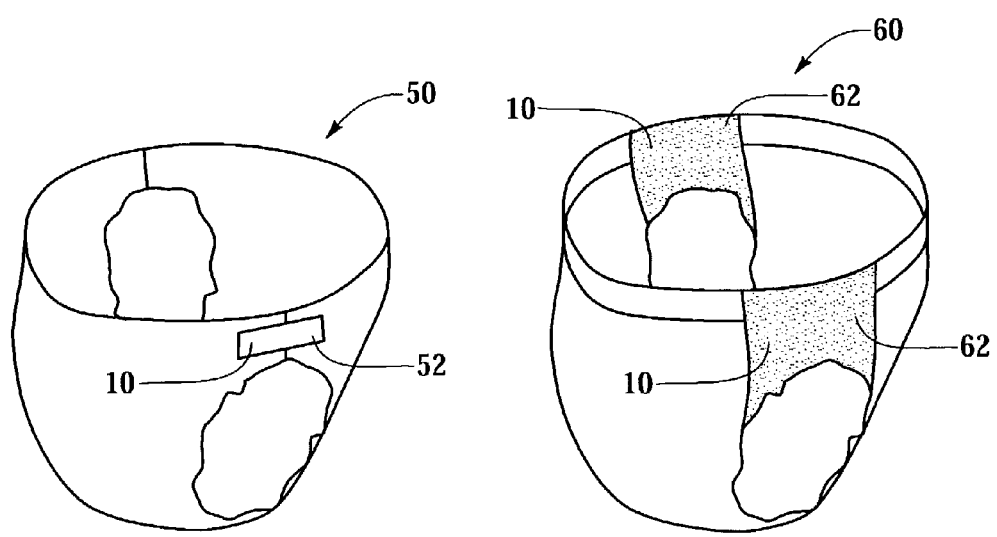
*Fig.5*  *Fig.6*

ABSORBENT ARTICLE WITH DOUBLE-SIDED SOFT AND ELASTIC COMPONENTS

This application claims benefit from U.S. Provisional Patent Application No. 60/334,913 filed Nov. 30, 2001.

FIELD OF THE INVENTION

The invention relates in general to absorbent and non-absorbent articles, and more particularly to absorbent and non-absorbent articles including an elastic component that is desired to be soft.

BACKGROUND

Designers of absorbent and non-absorbent articles strive to improve the tactile feel of materials, increase breathability of the article, and improve hand. Designers also desire to improve the fit of articles by incorporating elastic zones, panels, or other elastic components. However, materials that have a pleasing tactile feel and hand are generally non-elastic, and materials that are elastic generally do not have a pleasing tactile feel and hand. Therefore, a dichotomy exists between providing elasticity and providing a pleasing feel and hand.

U.S. Pat. Nos. 5,143,679, 5,156,793 and 5,167,897 to Weber et. al. describe methods for incrementally stretching a portion of an article constructed from a laminate of a non-elastic material having a pleasing tactile feel and an elastic material, the stretching to impart the laminate with elasticity. More particularly, Weber stretches the waistband portion of a diaper by passing the laminate between intermeshing gear rolls. When the stretching force is removed, the laminate retracts, causing the non-elastic layer to shir or bulk. The resulting laminate has limited elasticity. Because it is necessary for the fibers of the non-elastic layer to remain unbroken in order for them to shir or bulk, the elastic laminate stretches easily only up to the point where it was previously stretched. Thereafter, the laminate strongly resists additional stretching, because the non-elastic layer must be stretched for the laminate to continue stretching. Furthermore, the Weber laminate is not apertured or breathable.

Another laminate is described in U.S. Pat. Nos. 5,422,172, 5,592,690, 5,634,216, and 5,861,074 to Wu. In these patents, Wu describes a method that is very similar to the Weber method, except that Wu stretches an entire laminate web. The web is a laminate of an elastic layer that is extrusion laminated to a non-elastic nonwoven layer. The laminate web is stretched with intermeshed gear rolls, and thereafter, can elastically stretch up to 150% its original length. As with the Weber laminate, the Wu laminate bulks after stretching, indicating that the fibers remain unbroken. Therefore, the Wu laminate stretches easily only up to the point where it was originally stretched (here up to 150% of its original length), because it is limited by the unbroken fibers of the non-elastic nonwoven layer. The Wu laminate is not apertured.

In addition to feel and hand of the materials used in articles, it is often important that the materials be breathable. Breathability is less of a concern in side-tabs, elastic ear and other fasteners, such as those disclosed in U.S. Pat. No. 6,255,236, as it is in side panels, which conform intimately to the body of the wearer. Apertured or otherwise gas permeable elastic films permit breathability of the film while maintaining good conformability. Additionally, the breathable elastic layers permit evaporation of perspiration and increase the circulation of air within the absorbent article. Air circulation is particularly beneficial, as it reduces the sticky feeling experienced by many wearers during use. As elasticity is improved, the conformity of the article increases, and it thus becomes increasingly important that the article be breathable since air cannot escape between the article and the wearer's skin. Neither of the laminates disclosed in the Weber patents and the Wu patents are apertured.

Accordingly, there is a need for an improved elastic composite that is not limited by the non-elasticity of the layers, yet has a pleasing feel and hand. Furthermore, there is a need for an elastic composite with pleasing feel and hand, as well as breathability.

SUMMARY

The present invention is directed to a double sided soft and elastic composite. The composite comprises a first non-elastic cloth-like material, a second non-elastic cloth-like material, and an elastic layer between the first non-elastic cloth-like material and the second cloth-like material, the elastic film having an elongation at break of at least 50%, and the composite having an elasticity substantially equal to the elasticity of the elastic layer.

The invention is also drawn to an absorbent article having a composite, comprising a first non-elastic cloth-like material, a second non-elastic cloth-like material, an elastic layer located between the first non-elastic cloth-like material and the second non-elastic cloth-like material, the elastic layer having elongation at break of at least 50%, and the composite having elasticity substantially equal to the elasticity of the elastic layer.

The invention is also drawn to a non-absorbent article having a composite comprising a first non-elastic cloth-like material, a second non-elastic cloth-like material, an elastic layer between the first non-elastic cloth-like material and the second non-elastic cloth-like material, the elastic layer having an elongation at break of at least 50%, and the composite having an elasticity substantially equal to the elasticity of the elastic layer.

The invention also encompasses a method of making an elastic laminate, comprising bonding a first non-elastic cloth-like material to a first side of an elastic layer, bonding a second non-elastic cloth-like material to a second side of the elastic layer, passing the laminate through intermeshing gear rolls and breaking both the first non-elastic cloth-like material and the second non-elastic cloth like material.

BRIEF DESCRIPTION OF THE DRAWINGS

These and other features, aspects, and advantages of the present invention will be better understood with reference to the following description, claims, and drawings where:

FIGS. 1A and 1B are cross sectional views of two exemplary apertured, double sided soft and elastic composites constructed in accordance with the invention;

FIG. 2 is a cross sectional view of another exemplary double sided soft and elastic composite constructed in accordance with the invention;

FIG. 3A is a schematic of an exemplary manufacturing process for use in producing a double sided soft and elastic composite in accordance with the invention; FIG. 3B is a schematic of an alternate portion of the exemplary manufacturing process of FIG. 3A;

FIG. 4 is a schematic of another exemplary manufacturing process for use in producing a double sided soft and elastic composite in accordance with the invention;

FIG. 5 is an exemplary article incorporating fasteners constructed with a double sided soft and elastic composite in accordance with the invention;

FIG. 6 is an exemplary article incorporating side panels constructed with a double sided soft and elastic composite in accordance with the invention;

DETAILED DESCRIPTION OF THE EXEMPLARY EMBODIMENTS OF THE INVENTION

Definitions

Figure 7:
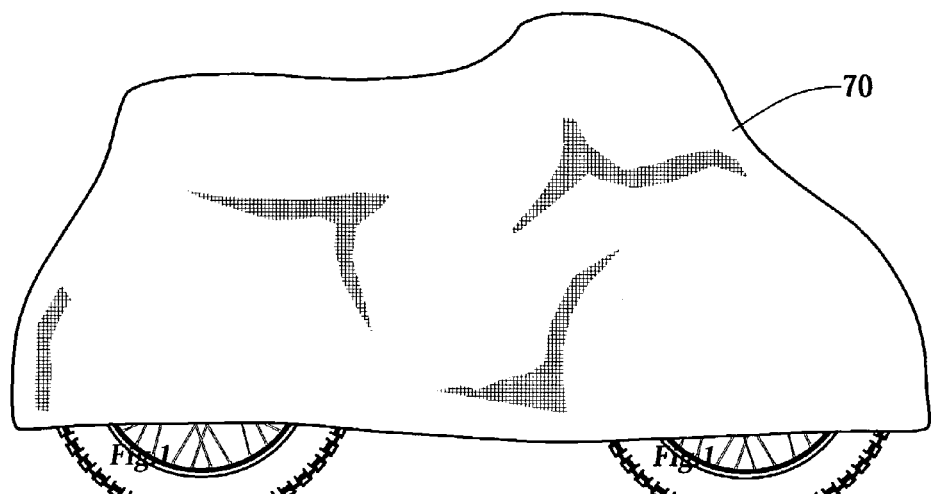
FIG. 7 is an exemplary non-absorbent article constructed with a double sided soft and elastic composite in accordance with the invention.

As used herein, the term "substantially" means that a given property or parameter may vary by at least about 20% from the stated value.

As used herein, the term "areas immediately surrounding the region of maximum fluid discharge" denotes a surface area surrounding the region of maximum fluid (e.g., liquid) and/or solid waste discharge and extending approximately 1 inch in all directions from that region. The terms "periphery," "peripheral areas" or "areas peripheral to" denote the surface area other than the area of maximum fluid discharge and the areas immediately surrounding it.

As used herein, the term "permeability" refers to the permeability of a material to a vapor or liquid.

As used herein, the term "ultrasonic bonding" means a process performed, for example, by passing the fabric between a sonic horn and an anvil roll such as illustrated in U.S. Pat. No. 4,374,888 to Bornslaeger or in U.S. Pat. No. 5,591,278 to Goodman et al. In an exemplary method of ultrasonic bonding, the various layers that are to be attached together are simultaneously fed to the bonding nip of an ultrasonic unit. A variety of these units are available commercially. In general, these units produce high frequency vibration energy that melt thermoplastic components at the bond sites within the layers and join them together. Therefore, the amount of induced energy, speed by which the combined components pass through the nip, gap at the nip, as well as the number of bond sites determine the extent of adhesion between the various layers. Very high frequencies are obtainable, and frequencies in excess of 18,000 cps (cycles per second) are usually referred to as ultrasonic, depending on the desired adhesion between various layers and the choice of material, frequencies as low as 5,000 cps or even lower may produce an acceptable product.

As used herein, the term "point bonding" means bonding one or more fabrics at a plurality of discrete points. For example, thermal point bonding generally involves passing one or more layers to be bonded between heated rolls, for example, an engraved pattern roll and a smooth calender roll. The engraved roll is patterned in some way so that the entire fabric is not bonded over its entire surface, and the calender roll is usually smooth. As a result, various patterns for engraved rolls have been developed for functional as well as aesthetic reasons.

As used herein, the term "barrier" means a film, laminate or other fabric which is substantially impermeable to the transmission of liquids and that preferably resists a hydrohead of at least 50 millibar (mbar) water. Hydrohead as used herein refers to a measure of the liquid barrier properties of a fabric. However, it should be noted that barrier fabrics of the invention can have a hydrohead value greater than 80 mbar, 150 mbar or even 300 mbar water.

As used herein, the term "breathable" refers to a material that is permeable to water vapor, preferably having a minimum water vapor transmission rate (WVTR) of about 300 $g/m^2/day$ (24 hours). The WVTR of a fabric gives an indication of how comfortable a fabric would be to wear. WVTR can be measured according to ASTM E96-00. Often, applications of breathable barriers typically have higher WVTRs, and breathable laminates of the present invention can have WVTRs exceeding about 800 $g/m^2/day$, 1500 $g/m^2/day$, or even exceeding 3000 $g/m^2/day$.

As used herein, "monolithically breathable" refers to a material that is breathable at least in part because of its chemical composition.

As used herein, the term "extensible" refers to a material that, upon application of a biasing force, is elongatable or stretchable in at least one direction.

As used herein, the term "elastic" means a material which, upon application of a biasing force, is stretchable, that is extensible, to a stretched, biased length preferably at least 150% of its relaxed unbiased length, and that will retract at least 50% of its elongation upon release of the elongating force.

As used herein, the term "set" means the amount of stretch remaining after removal of a biasing force expressed as a percentage of the original length: Permanent set (%)=((Final length−Original length)×100)/Original length.

A hypothetical example would be a 1.00 inch long sample of a material which is elongatable to 1.50 inches and which, upon release of the biasing force, will retract to a length of 1.25 inches. This sample has a 25% "set".

As used herein, the terms "inelastic" and "non-elastic" refer to any material which does not fall within the definition of "elastic" above.

As used herein, the term "garment" means any type of apparel that is intended to be worn. This includes, among other things, industrial work wear and coveralls, undergarments, pants, shirts, jackets, gloves, socks, and the like.

As used herein, the term "infection control product" means medically oriented items, and includes, among other things, surgical gowns and drapes, face masks, head coverings like bouffant caps, surgical caps and hoods, footwear like shoe coverings, boot covers and slippers, wound dressings, bandages, sterilization wraps, wipes, garments like lab coats, coveralls, aprons and jackets, patient bedding, stretcher and bassinet sheets, and the like.

As used herein, the term "protective cover" means a cover for various items, for example, vehicles such as cars, trucks, boats, airplanes, motorcycles, bicycles, golf carts, etc., covers for equipment often left outdoors like grills, yard and garden equipment (mowers, roto-tillers, etc.) and lawn furniture, as well as floor coverings, table cloths and picnic area covers.

As used herein, the term "absorbent articles" means articles that absorb and contain body fluids and other body exudates. More specifically, an absorbent article includes garments that are placed against or in proximity to the body of a wearer to absorb and contain the various exudates discharged from a body. A non-exhaustive list of examples includes diapers, training pants, absorbent underpants, adult incontinence products, and feminine hygiene products.

As used herein, the term "non-absorbent articles" means articles that are not intended to be used for absorbing fluids. A non-exhaustive list of examples includes garments, protective covers, and infection control products.

As defined herein, "draw ratio" or "l/w" is the ratio of the deformed length over the original length of a drawn sample. In the context of an intermeshing gear device (IMG), it is the distance between the centerline of the gear teeth "w" and the longest length experienced by the laminate while it is stretched between the gear teeth "l", which occurs at the maximum depth of engagement. An equivalent definition is:

Draw ratio=Deformed length/Original length

As defined herein "percent elongation" is:

Percent elongation=(Increase in sample length×100)/Original length or Percent elongation=(Draw ratio−1)×100.

Description of the Exemplary Embodiments

Referring first to FIG. 1A, a double-sided soft and elastic composite 10 for use in an absorbent or non-absorbent article is depicted. The double-sided soft and elastic composite 10 has a first non-elastic material 12 on one surface of an elastic layer 14, and a second non-elastic material 16 on an opposed surface of the elastic layer 14.

In one exemplary embodiment, the elastic layer 14 is a co-extruded film having a an elastic core 18, a first skin layer 20 and a second skin layer 22 on the outer surfaces of the elastic core 18. It is, however, within the scope of the invention to use other elastic layer configurations. The elastic layer 14 can have an elongation at break ranging from 50% to greater than 700%.

If it is desired that the composite 10 be breathable, the elastic layer 14 can have apertures 24 that pass through both the elastic core 18 and the skin layers 20, 22. FIGS. 1A and 1B depict exemplary composites 10 having apertures 24. FIG. 2 depicts an alternate exemplary embodiment where composite 10 has no apertures. The elastic layer 14 can also be constructed from a non-breathable material and filler material (such as calcium carbonate, talc or other materials known in the art) made breathable by stretching it to create interconnecting voids around the filler particles, or a monolithically breathable material, so that an unapertured embodiment, such as in FIG. 2, may still be breathable.

The elastic layer 14 can be made from any suitable elastic materials like natural or synthetic polymeric materials. Examples of suitable polymers include low crystallinity polyethylenes, metallocene catalyzed low crystallinity polyethylene, ethylene vinyl acetate copolymers (EVA), polyurethane, polyisoprene, butadiene-styrene copolymers, styrene block copolymers such as styrene/isoprene/styrene (SIS), styrene/butadiene/styrene (SBS), or styrene/ethylene-butadiene/styrene (SEBS) block copolymers. Blends of these polymers alone or with other modifying elastic or non-elastomeric materials are also contemplated being useful with the present invention. In certain preferred embodiments, the elastomeric materials can comprise high performance elastomeric materials such as elastomeric block copolymers. An example of a suitable elastomeric block copolymer is sold under the brand name KRATON, a registered trademark of the Shell Oil Company Corporation.

The non-elastic materials 12, 16 are chosen to provide a cloth-like feel, that is, a fibrous feel that is soft and/or silky. It is not necessary for the non-elastic materials 12, 16, though, to be fibrous to provide a cloth-like feel. In the exemplary embodiment, the non-elastic materials 12, 16 are either carded or spunbonded nonwoven webs. However, it is within the scope of the invention to utilize other non-elastic materials, including but not limited to melt blown and air laid nonwoven webs and woven fabrics.

The non-elastic materials can be made from any suitable materials. A non-exhaustive list of suitable materials includes polyester, polyethylene, polypropylene, and other polyolefin homopolymers and copolymers, acrylic polymer resins and multilayer mixtures thereof, rayon, cotton, cellulose, and blends of any of the above. In one exemplary embodiment, the first non-elastic material 12 is chosen to have a different elongation at break than the elongation at break of the second non-elastic material 16. The remaining properties may be substantially the same.

Referring to FIG. 3, exemplary methods of making the composite 10 of the invention will now be discussed. In making the composite 10, the elastic layer 14 is extruded (in a single component elastic layer 14) or co-extruded (in an elastic layer 14 having a core 18 and skin layers 20, 22) from a film die 30 into a bonding stage 32a or 32b where the first non-elastic material 12 is bonded to the elastic layer 14. The first non-elastic material 12 can be affixed to the elastic layer 14 using various techniques known in the art. Bonding stage 32a is a vacuum lamination process, such as the vacuum lamination process described in U.S. Pat. No. 5,733,628 to James Pelkie, and can be used to produce a three-dimensional, apertured elastic layer 14 as shown in FIG. 1A. In accordance with the method disclosed in Pelkie, the elastic layer 14 in a molten or semi-molten state is passed over a vacuum lamination drum 34, for example a vacuum screen, together with the first non-elastic material 12. The first non-elastic material 12 is brought into contact with a surface of the elastic layer 14 by an impingement roll 36. Low pressure within the vacuum lamination drum 34 pulls portions of the elastic layer 14 partially into the drum 34. The portions pulled into the drum 34 impart a three-dimensional shape to the elastic layer 14 (rather than its as-extruded substantially planar, 2-dimensional shape) and eventually rupture to form apertures 24 (shown in FIG. 1A). After the elastic layer 14 is apertured, the low pressure within the drum 34 also holds the first non-elastic material 12 in contact with the elastic material 14 as elastic layer 14 cools, thereby enabling the first non-elastic material 12 to bond to the elastic layer 14. No adhesive is needed. Using the bonding stage 32a, creates a breathable, three-dimensional composite 10.

Alternatively, the first non-elastic material 12 may be placed in contact with the vacuum lamination drum 34, and the molten or semi-molten elastic layer 14 coated onto the non-elastic material 12 opposite the vacuum lamination drum 34. In this case, no apertures are formed in the elastic layer 14 and the composite 10 will resemble FIG. 2.

In an alternate bonding stage 32b, the first non-elastic material 12 and elastic material 14 are bonded using a point-bonding system, such as a thermal or ultrasonic system, an adhesive, or by other methods known in the art. In each of these systems, the elastic layer 14 is brought into contact with the first non-elastic material 12 with rollers 38. Rollers 38 may be a patterned roller and smooth roller (i.e. thermal bonding), sonic horn and anvil roller (i.e. ultrasonic bonding), or other types of rollers. Using bonding stage 32b does not necessarily create a breathable or three-dimensional composite 10, because the bonding processes of bonding stage 32b do not involve aperturing the elastic layer 14 or forming the elastic layer 14 into a three-dimensional shape. If it is desired to achieve a three-dimensional elastic layer 14 and/or an apertured elastic layer 14, separate forming and/or aperturing processes must be performed. For example, the elastic layer 14 can be apertured mechanically, such as by piercing the elastic layer with heated or un-heated pins (discussed below).

In an exemplary method, the second non-elastic material 16 is introduced into contact with a surface of the bonded elastic layer 14 opposite the surface on which the first non-elastic material 12 is bonded. The second non-elastic material 16 can be bonded to the elastic layer 14 adhesively, by a point bonding method such as thermal or ultrasonic bonding, or by other methods known in the art.

Referring briefly to FIG. 4, one or both of the first non-elastic material 12 and second non-elastic material 16 can be extrusion laminated with the elastic layer 14. In an extrusion lamination process, the elastic layer 14 is extruded into the nip of rollers 40 together with one or both of the first non-elastic material 12 and second non-elastic material 16. Because the elastic layer 14 is molten or semi-molten it bonds with the first non-elastic material 12 and/or second non-elastic material 16 as it cools. Furthermore, one or both rollers 40 may be chilled to quench the elastic layer 14. As with the bonding stage 32b, extrusion lamination does not impart apertures or a three-dimensional shape to the elastic layer 14. Therefore, if it is desired that the elastic layer 14 have a three-dimensional shape and/or apertures, separate forming and/or aperturing processes must be performed. FIG. 4 also depicts an exemplary process for aperturing the composite using heated or un-heated pins that pierce the composite 10. The resulting composite 10 will resemble FIG. 1B.

Referring again to FIG. 3, after the first non-elastic material 12 and the second non-elastic material 16 are bonded to the elastic layer 14, the composite 10 is stretched to break the non-elastic materials 12, 16. FIG. 3 depicts stretching the composite 10 using heated or un-heated intermeshing gear rollers (IMG) 42; however, other methods of stretching the composite 10, such as machine direction orientation (MDO) and tentering, are also acceptable. The IMG rollers 42 have circumferentially oriented teeth (not specifically shown) that intermesh and thereby stretch the composite 10 as it passes through the rollers 42. The direction of movement of the composite 10 through the IMG rollers 42 is commonly referred to as the machine direction. The IMG rollers 42 stretch the composite 10 and break the first non-elastic material 12 and second non-elastic material 16 in a direction substantially perpendicular to the machine direction, in other words, the transverse direction. It is within the scope of this invention to alternately stretch the composite 10 and break the non-elastic materials 12, 16 in the machine direction. Also, limited portions of the composite 10 can be stretched independently to create local zones of elastically recoverable material.

In an embodiment where the first non-elastic material 12 has a different elongation to break than the second non-elastic material 16, one non-elastic will break before the other as the composite 10 is stretched. Because the non-elastic materials 12, 16 do not break simultaneously, the maximum force needed to stretch the composite 10 and break the non-elastic layers is less than it would be if the non-elastic layers broke at the same elongation. This is desirable in that many stretching devices, for example IMG rollers 42, may not be able to apply the force necessary to break both the first non-elastic material 12 and second non-elastic material 16 simultaneously.

The resulting composite 10 is both soft and elastic. Because of the broken non-elastic materials, the composite 10 can elongate past the point of incremental elongation and is not limited by the stretch modulus of the non-elastic materials. In other words, the elongation of the laminate will depend primarily on the elastic layer, and therefore will elongate substantially beyond the draw ratio achieved by the intermeshing gears.

FIG. 5 depicts an exemplary article 50 incorporating the double sided soft and elastic composite 10 of the invention in fasteners 52. The fasteners 52 are provided to at least partially secure the article about a wearer's body. While the figure depicts a diaper or adult incontinent article using fasteners 52 of a particular configuration, it is within the scope of the invention to use the composite 10 in other configurations of fasteners in other absorbent and non-absorbent articles.

FIG. 6 depicts another exemplary article 60 incorporating the double sided soft and elastic composite 10 of the invention as elastic side panels 62. The side panels 62 allow the article to flex and at least partially conform to a wearer's body. Additionally, the composite 10 can be configured to be breathable, by including apertures 24 (best seen in FIG. 1A or 1B) or monolithically breathable materials, thereby increasing the comfort of the wearer by allowing airflow through the side panels 62. While the figure depicts a diaper or adult incontinent article using side panels 62 of a particular configuration, it is within the scope of the invention to use the composite 10 in other configurations of side panels in other absorbent and non-absorbent articles.

FIG. 7 depicts an exemplary non-absorbent article 70, in this case a protective cover for a vehicle, incorporating the double sided soft and elastic composite 10. When used in a non-absorbent article, the composite 10 may be configured to be breathable, by including apertures 24 (best seen in FIG. 1A or 1B), by including monolithically breathable materials, or by including a non-breathable material and filler material and stretching it to create interconnecting voids around the filler particles. The non-absorbent article 70 can be constructed of a single layer of the composite 10 or multiple layers including layers of the composite 10 and other materials. While the figure depicts a protective cover, it is within the scope of the invention to use the composite 10 in other non-absorbent articles.

Figure 8:
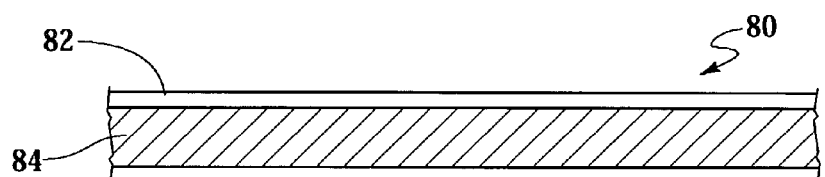
FIG. 8 is a cross section of an exemplary absorbent article constructed with a double sided soft and elastic composite in accordance with the invention.
Figure 9:
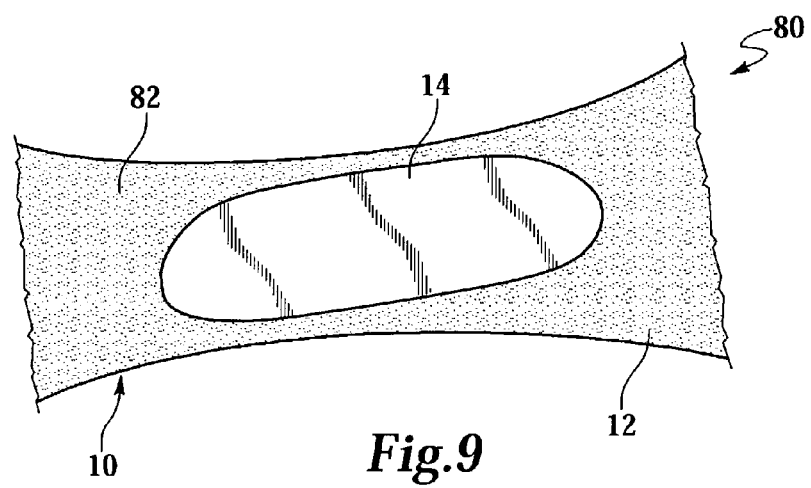
FIG. 9 is a view of a topsheet of an absorbent article constructed with a double sided soft and elastic composite in accordance with the invention.

FIG. 8 depicts a cross sectional view of an exemplary absorbent article 80. The absorbent article 80 has at least a topsheet 82 positioned to face the wearer, an absorbent core 84, and a backsheet 86 positioned to face away from the wearer. Other layers may be included in this construction; however, only the topsheet 82, absorbent core 84, and backsheet 86 are shown for clarity. The double sided soft and elastic composite 10 can be incorporated in either the topsheet 82 or backsheet 86 alone or in combination with other films. As a backsheet 86 it is desirable, though not necessary, that the composite 10 be apertured. As a topsheet 82, the composite 10 should have apertures 24 (best seen in FIG. 1) to allow exudates to pass into the absorbent core 84. Optionally, as shown in FIG. 9, in a topsheet 82, the first non-elastic material 12 can be omitted immediately around the area of maximum fluid discharge in order to maximize the fluid transmission of the elastic layer 14, while maintaining the soft feel of the non-elastic material 12 in remaining areas.

Illustrative Examples

Example 1 is a composite constructed with a first layer (first non-elastic material) that is a 15 gsm (grams per square meter) spunbonded non-woven material from BBA Nonwovens, commercially available as FPN-639. The second layer (elastic layer) is a 68.6 μm (2.7 mil) thick co-extruded apertured elastic layer having two 3.8 μm (0.15 mil) thick non-elastic polyethylene skin layers and a 61.0 μm (2.4 mil) thick elastic core. The apertures are arranged in a square array with 787.4 holes per linear meter in a square pattern (619,998.8 holes per square meter, 20 mesh, 20 holes per linear inch, 400 holes per square inch) that provides an open area of approximately 10%. The third layer (second non-elastic layer) is a 20 gsm carded non-woven from BBA Nonwovens, commercially available as FPN-337D. The first and second layers are bonded using the vacuum lamination process according to the teachings of the Pelkie patent. The bi-laminate (the first and second layers) is then bonded to the third layer in an adhesive lamination process using pressure sensitive hot melt adhesive commercially available from National Starch Company, as Easy Melt 34-563 A. The laminate is stretched by passing it once between a pair of circumferentially grooved intermeshing gear rolls that provide a 4.60 draw ratio (360% elongation) at a speed of 30.5 mpm (meters per minute) (100 fpm (feet per minute)).

Example 2 consists of the same materials as example 1 and was made using the same processes as example 1, except that the intermeshing gear rolls were operated at a surface speed of 15.2 mpm (50 fpm).

Incremental stretching to break the fibers of the first and third layers achieved an unanticipated result in that both laminates can withstand elongation of greater than 700% without experiencing tearing, or other failure, of the elastic layer.

The elastic properties of the resulting laminates are shown in Table 1. For reference, the test methods used to measure the values in Tables 1-5 are set forth below.

Tensile properties (tensile strength at break, elongation at break and elongation at 198 N/m load) were determined by stretching a specimen 25.4 mm (1.00 in) wide with a gauge length of 50.8 mm (2.00 in) at 50.8 mm/min (2.00 in/min) using line grips.

"Load@100%" and "Load@30% Rc2" were both measured in the transverse direction. "Load@30% Rc2" is the load sustained by a sample 25.4 mm (1.00 in) wide with a gauge length of 25.4 mm (1.00 in) after the following stretching sequence. The sample is stretched to 500% strain at 12.7 mm/min (0.50 in/min), immediately allowed to relax at 12.7 mm/min (0.50 in/min) to 0% extension, and held at 0% extension for 60 seconds. The sample is then stretched to 200% strain at 254 mm/min (10.00 in/min), held at 200% strain for 30 seconds, and then allowed to relax at 254 mm/min (10.00 in/min) to 0% extension and held for 30 seconds. Thereafter, the sample is stretched to 200% strain at 254 mm/min (10.00 in/min), held at 200% strain for 30 seconds, and allowed to relax at 254 mm/min (10.00 in/min). The load at 30% strain is then noted.

Permanent set is obtained by stretching a sample 25.4 mm (1.00 in) wide with a gauge length of 25.4 mm (1.00 in) to 200% elongation at 254 mm/min (10.00 in/min), holding the sample at 200% elongation at 30 seconds, allowing the sample to relax to 254 mm/min (10.00 in/min) to 0% extension, holding the sample at 0% extension for 30 seconds, then stretching the sample at 254 mm/min (10.00 in/min). The permanent set is recorded at the elongation at which a non-zero load is measured.

TABLE 1

| Example | 1 | 2 |
|---|---|---|
| Elastic layer thickness (μm) | 68.6 | 68.6 |
| Surface speed (mpm) | 30.5 | 15.2 |
| Tensile strength at break TD (N/m) | 764 | 870 |
| Elongation at break TD (%) | 786 | 778 |
| TD Elongation @ 193 N/m load (%) | 218 | 213 |
| Load @ 100% (N/m) | 63.0 | 71.7 |
| Load @ 30% Rc2 (N/m) | 3.5 | 5.5 |
| Set (%) | 8.7 | 7.0 |

Example 3 has the same materials as example 1 and was made using the same processes as example 1, except that the thickness of the elastic core was reduced from 61.0 to 53.3 μm (2.4 to 2.1 mil), thus reducing the thickness of the elastic layer to 61.0 μm (2.4 mil).

Example 4 has the same materials as example 1 and was made using the same processes as example 1, except that the thickness of the elastic core was increased from 61.0 to 71.1 μm (2.4 to 2.8 mil), thus increasing the thickness of the elastic layer to 78.7 μm (3.1 mil). The draw ratio was 4.28 (328%) (vs. 4.60 (360%) of example 1) and the intermeshing gear rolls were operated at a surface speed of 15.2 mpm (50 fpm).

Incremental stretching to break the fibers of the first and third layers achieved an unanticipated result in that both laminates can withstand an elongation of greater than 700%.

The elastic properties of the resulting laminates are shown in Table 2 below:

TABLE 2

| Example | 3 | 4 |
|---|---|---|
| Elastic layer thickness (μm) | 61.0 | 78.7 |
| Surface speed (mpm) | 30.5 | 15.2 |
| Draw ratio | 4.60 | 4.28 |
| Tensile strength at break TD (N/m) | 803 | 937 |
| Elongation at break TD (%) | 815 | 778 |
| TD Elongation @ 193 N/m load (%) | 212 | 196 |
| Load @ 100% (N/m) | 64.6 | 78.3 |
| Load @ 30% Rc2 (N/m) | 4.7 | 7.5 |
| Set (%) | 7.8 | 5.3 |

Comparative example 5 is a laminate of a first layer that is a 20 gsm carded nonwoven from BBA Nonwovens, commercially available as FPN-337D, a second layer that is a 78.7 μm (3.1 mil) thick co-extruded apertured elastic layer having two 3.8 μm (0.15 mil) thick non-elastic polyethylene skin layers and a 71.1 μm (2.8 mil) elastic core, and a third layer of a 20 gsm carded nonwoven from BBA Nonwovens, commercially available as FPN-337D. The apertures of the second layer are arranged in a square array with 787.4 holes per linear meter that provides an open area of approximately 10%. The first and second layers are bonded in a vacuum lamination process according to the teachings of the Pelkie patent. The bi-laminate is then bonded to the third layer in an adhesive lamination process using pressure-sensitive hot melt adhesive commercially available from National Starch Company, as Easy Melt 34-563 A. The laminate is stretched by passing it once between a pair of circumferentially grooved intermeshing gear rolls that provide a 4.28 draw ratio (328% elongation) at a speed of 15.2 mpm (50 fpm). The difference between examples 4 and 5 is that both cloth-like layers in comparative example 5 are 20 gsm carded nonwovens, whereas in example 4 the first layer is a 15 gsm spunbonded nonwoven.

Comparative example 6 has the same materials as example 5 and was made using the same processes as example 5, except that 24 gsm nonwoven material was used (BBA FPN-333D) as the first and third layers.

The elastic properties of the resulting laminates are shown in Table 3 below:

TABLE 3

| Example | 4 | Comparative 5 | Comparative 6 |
|---|---|---|---|
| Cloth-like layer 1 | 15 gsm spun | 20 gsm carded | 24 gsm carded |
| Cloth-like layer 2 | 20 gsm carded | 20 gsm carded | 24 gsm carded |
| Tensile strength at break TD (N/m) | 937 | 1035 | 996 |

TABLE 3-continued

| Example | 4 | Comparative 5 | Comparative 6 |
|---|---|---|---|
| Elongation at break TD (%) | 778 | 797 | 780 |
| TD Elongation @ 193 N/m load (%) | 196 | 147 | 142 |
| Load @ 100% (N/m) | 78.3 | 90.9 | 95.3 |
| Load @ 30% Rc2 (N/m) | 7.5 | 7.5 | 7.1 |
| Set (%) | 5.3 | 6.3 | 6.7 |

Comparative example 7 is made from the same materials and processes as example 2, with the exception that it was not stretched—the test samples were measured un-stretched. As the data shows, this sample has the highest TD elongation at break of all the samples. This is an indication that some degree of damage occurs in the stretching process. The data also shows that the TD elongation % at 193 N/m of load was extremely low. This is consistent with an un-stretched sample and is a clear indication of the value of the invention which is to create highly elastic soft materials that stretch without requiring large forces to stretch.

Comparative example 8 is similar to example 2 except that the second layer of cloth-like material is a 15 gsm spun-bonded nonwoven (FPN-639). The draw ratio achieved with this sample is less than the draw ratio achieved with other samples because the intermeshing gears would not turn at a depth of engagement greater than 2.67 mm (105 mils) (vs. 3.30 mm (130 mils)). This is proof of the value of the invention with regard to use of cloth-like materials with substantially different break points. In this case, because the elongations at break are not substantially different, the equipment is stressed and in some cases will not work at all. If a high draw ratio cannot be achieved, the resulting composite will exhibit a low TD elongation at 193 N/m load.

The properties of the resulting laminates are shown in Table 4 below:

TABLE 4

| Example | 2 | Comparative 7 | Comparative 8 |
|---|---|---|---|
| Cloth-like layer 1 | 15 gsm carded | 15 gsm carded | 15 gsm spun |
| Cloth-like layer 2 | 20 gsm spun | 20 gsm spun | 15 gsm spun |
| Draw ratio | 4.60 | 1.00 | 3.79 |
| Tensile strength at break TD (N/m) | 870 | 913 | 933 |
| Elongation at break TD (%) | 778 | 905 | 774 |
| TD Elongation @ 193 N/m load (%) | 213 | 28 | 91 |
| Load @ 100% (N/m) | 71.7 | 399.2 | 253.5 |
| Load @ 30% Rc2 (N/m) | 5.5 | 0.4 | 3.1 |
| Set (%) | 7.0 | 18.3 | 8.0 |

Comparative example 9 is a film only sample (i.e. the elastic film with no non-elastic cloth-like layers) made from the same materials as the elastic layer in example 1. The thickness of the elastic core is 53.3 μm (2.1 mil) with skins 3.8 μm (0.15 mil) thick, for a total thickness of 61.0 μm (2.4 mil) compared to 68.6 μm (2.7 mil) for example 1. Comparative example 9 was not stretched between intermeshing gear rolls prior to testing. Data for comparative example 9 and example 1 are shown in Table 5 below. Differences between example 1 and comparative example 9 can be readily understood in terms of the invention and differences in elastic layer thickness and processing differences. The tensile strength and elongation at break of comparative example 9 are somewhat higher than that of example 1, indicative of the working of the elastic layer of example 1 by the intermeshing gear rolls. TD elongation@193 N/m for comparative example 9 is substantially greater than that of example 1; the difference is attributable to the residual strength of nonwoven after stretching between the intermeshing gear rolls. Load at 100% elongation for comparative example 9 is substantially higher than that of example 1, because its skins had not been stretched by passing it between intermeshing gear rolls. Load@30% Rc2 for example 1 is slightly higher than that of comparative example 9, mainly because the elastic layer of example 1 is thicker than comparative example 9.

TABLE 5

| Example | 1 | Comparative 9 |
|---|---|---|
| Elastic layer thickness (μm) | 68.6 | 61.0 |
| Tensile strength at break TD (N/m) | 764 | 893 |
| Elongation at break TD (%) | 786 | 897 |
| TD Elongation @ 193 N/m load (%) | 218 | 452 |
| Load @ 100% (N/m) | 63.0 | 94.5 |
| Load @ 30% Rc2 (N/m) | 3.5 | 2.0 |
| Set (%) | 8.7 | 5.0 |

Although the present invention has been described in considerable detail with reference to certain exemplary embodiments thereof, other versions are possible. Therefore, the spirit and scope of the appended claims should not be limited to the description of the exemplary embodiments contained herein.

We claim:

1. An absorbent article having a composite, the composite comprising:
    a first broken non-elastic cloth-like material having a first elongation at break;
    a second broken non-elastic cloth-like material having a second elongation at break, wherein said second elongation at break is substantially different from said first elongation at break; and
    an elastic layer located between the first broken non-elastic cloth-like material and the second broken non-elastic cloth-like material, the elastic layer having an elongation at break of at least 50%.

2. The absorbent article of claim 1 wherein said composite has an elasticity substantially equal to the elasticity of said elastic layer.

3. The absorbent article of claim 1 wherein said composite has a retractability substantially equal to the retractability of said elastic layer.

4. The absorbent article of claim 1 wherein the composite is incorporated into at least one of a topsheet, a backsheet, a fastener, a waistband, a side panel, and a leg cuff.

5. The absorbent article of claim 1 wherein the elastic layer is breathable.

6. The absorbent article of claim 1 wherein the elastic layer comprises a monolithically breathable material.

7. The absorbent article of claim 1 wherein the elastic layer comprises a composite material including a non-breathable material and a stretched filler having interconnecting voids.

8. The absorbent article of claim 1 wherein the elastic layer comprises a three-dimensional apertured film.

9. The absorbent article of claim 1 wherein the elastic layer comprises a two-dimensional apertured film.

10. The absorbent article of claim 1 wherein the first or second broken non-elastic cloth-like material comprises a nonwoven material.

11. The absorbent article of claim 1 wherein the elastic layer comprises:
- a first non-elastic skin layer;
- a second non-elastic skin layer; and
- an elastic core between the first and second skin layers.

12. A non-absorbent article including a composite comprising:
- a first broken non-elastic cloth-like material having a first elongation at break;
- a second broken non-elastic cloth-like material having a second elongation at break, wherein said second elongation at break is substantially different from said first elongation at break; and
- an elastic layer located between the first broken non-elastic cloth-like material and the second broken non-elastic cloth-like material, the elastic layer having an elongation at break of at least 50%.

13. The non-absorbent article of claim 12 wherein said composite has an elasticity substantially equal to the elasticity of said elastic layer.

14. The non-absorbent article of claim 12 wherein said composite has a retractability substantially equal to the retractability of said elastic layer.

15. The non-absorbent article of claim 12 wherein the elastic layer is breathable.

16. The non-absorbent article of claim 12 wherein the elastic layer comprises a monolithically breathable material.

17. The non-absorbent article of claim 12 wherein the elastic layer comprises a non-breathable material and a stretched filler having interconnecting voids.

18. The non-absorbent article of claim 12 wherein the elastic layer comprises a three-dimensional apertured film.

19. The non-absorbent article of claim 12 wherein the elastic layer comprises a two-dimensional apertured film.

20. The non-absorbent article of claim 12 wherein the first or second broken non-elastic cloth-like material comprises a nonwoven material.

21. An elastic composite comprising:
- a first broken non-elastic cloth-like material having a first elongation at break;
- a second broken non-elastic cloth-like material having a second elongation at break, wherein said second elongation at break is substantially different from said first elongation at break; and
- an elastic layer located between the first broken non-elastic cloth-like material and the second broken non-elastic cloth-like material, the elastic layer having an elongation at break of at least 50%.

22. The composite of claim 21 wherein said composite has an elasticity substantially equal to the elasticity of said elastic layer.

23. The composite of claim 21 wherein said composite has a retractability substantially equal to the retractability of said elastic layer.

24. The composite of claim 21 wherein the first broken non-elastic cloth-like material has an elongation at break substantially different from the elongation at break of the second broken non-elastic cloth-like material.

25. The composite of claim 21 wherein the elastic layer is breathable.

26. The composite of claim 21 wherein the elastic layer comprises a monolithically breathable material.

27. The composite of claim 21 wherein the elastic layer comprises a non-breathable material and a stretched filler having interconnecting voids.

28. The composite of claim 21 wherein the elastic layer comprises a three-dimensional apertured film.

29. The composite of claim 21 wherein the elastic layer comprises a two-dimensional apertured film.

30. An absorbent article having a composite, the composite comprising:
- a first broken non-elastic cloth-like material having a first elongation at break;
- a second broken non-elastic cloth-like material having a second elongation at break, wherein said second elongation at break is substantially different from said first elongation at break; and
- an elastic layer located between the first broken non-elastic cloth-like material and the second broken non-elastic cloth-like material, the elastic layer having an elongation at break of at least 50%, wherein the elastic layer comprises:
- a first non-elastic skin layer;
- a second non-elastic skin layer; and
- an elastic core between the first and second skin layers.

31. The absorbent article of claim 30 wherein said composite has an elasticity substantially equal to the elasticity of said elastic layer.

32. The absorbent article of claim 30 wherein said composite has a retractability substantially equal to the retractability of said elastic layer.

33. The absorbent article of claim 30 wherein the composite is incorporated into at least one of a topsheet, a backsheet, a fastener, a waistband, a side panel, and a leg cuff.

34. The absorbent article of claim 30 wherein the elastic layer is breathable.

35. The absorbent article of claim 30 wherein the elastic layer comprises a monolithically breathable material.

36. The absorbent article of claim 30 wherein the elastic layer comprises a composite material including a non-breathable material and a stretched filler having interconnecting voids.

* * * * *